(12) United States Patent
Aalders et al.

(10) Patent No.: US 10,987,455 B2
(45) Date of Patent: Apr. 27, 2021

(54) BREAST PUMP, METHOD AND COMPUTER PROGRAM

(71) Applicant: KONINKLIJKE PHILIPS N.V., Eindhoven (NL)

(72) Inventors: Arnold Aalders, Eindhoven (NL); Arjan Teodor Van Wieringen, Eindhoven (NL); Hassan El Barakat, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 271 days.

(21) Appl. No.: 16/064,638

(22) PCT Filed: Dec. 15, 2016

(86) PCT No.: PCT/EP2016/081109
§ 371 (c)(1),
(2) Date: Jun. 21, 2018

(87) PCT Pub. No.: WO2017/108555
PCT Pub. Date: Jun. 29, 2017

(65) Prior Publication Data
US 2018/0369464 A1    Dec. 27, 2018

(30) Foreign Application Priority Data
Dec. 23, 2015   (EP) .................................. 15202295

(51) Int. Cl.
*A61M 1/00*     (2006.01)
*A61M 1/06*     (2006.01)
(Continued)

(52) U.S. Cl.
CPC ............ *A61M 1/06* (2013.01); *A61M 1/0025* (2014.02); *A61M 1/0031* (2013.01);
(Continued)

(58) Field of Classification Search
CPC ........ A61M 1/06; A61M 1/062; A61M 1/064; A61M 1/0049; A61M 2205/50;
(Continued)

(56) References Cited

U.S. PATENT DOCUMENTS

| 6,840,918 B1 * | 1/2005 | Britto ...................... A61M 1/06 604/364 |
| 2009/0099511 A1 * | 4/2009 | Sutrina ................... A61M 1/06 604/74 |

(Continued)

FOREIGN PATENT DOCUMENTS

| EP | 1430918 A1 | 6/2004 |
| WO | 1995031096 A1 | 11/1995 |

(Continued)

*Primary Examiner* — Nathan R Price
*Assistant Examiner* — Tania Ismail

(57) ABSTRACT

The present invention relates to a breast pump (1) for extracting milk from a female breast comprising an expression kit (2), a container (5) connected to the expression kit (2), and a vacuum unit (6) connected to the expression kit (2), wherein the combined volumes of the expression kit (2), the container (5), the vacuum unit (6) and the connections thereof define a system air volume, and a vacuum pressure sensor for determining volume changes in the system air volume in response to changes in vacuum pressure.

18 Claims, 2 Drawing Sheets

(51) Int. Cl.
*F04B 43/06* (2006.01)
*F04B 43/073* (2006.01)

(52) U.S. Cl.
CPC ....... *A61M 1/0072* (2014.02); *A61M 2205/33* (2013.01); *A61M 2205/3327* (2013.01); *A61M 2205/3331* (2013.01); *A61M 2205/3334* (2013.01); *A61M 2205/3379* (2013.01); *A61M 2205/50* (2013.01); *A61M 2205/52* (2013.01); *F04B 43/06* (2013.01); *F04B 43/073* (2013.01)

(58) Field of Classification Search
CPC .. A61M 2205/3334; A61M 2205/3331; A61M 2205/3344
See application file for complete search history.

(56) References Cited

U.S. PATENT DOCUMENTS

| | | | |
|---|---|---|---|
| 2011/0004154 A1 | 1/2011 | Van Schijndel | |
| 2012/0004603 A1* | 1/2012 | Harari | A61B 5/1075 604/74 |
| 2015/0065994 A1 | 3/2015 | Fridman | |
| 2015/0112298 A1 | 4/2015 | Pirzada | |

FOREIGN PATENT DOCUMENTS

| | | |
|---|---|---|
| WO | 2010095133 A1 | 8/2010 |
| WO | 2015120321 A1 | 8/2015 |
| WO | 2016014469 A1 | 1/2016 |
| WO | 2016014488 A1 | 1/2016 |

\* cited by examiner

BREAST PUMP, METHOD AND COMPUTER PROGRAM

This application is the U.S. National Phase application under 35 U.S.C. § 371 of International Application No. PCT/EP2016/081109, filed on Dec. 15, 2016, which claims the benefit of International Application No. 15202295.0 filed on Dec. 23, 2016. These applications are hereby incorporated by reference herein.

FIELD OF THE INVENTION

The present invention relates to a breast pump with a functionality which allows monitoring of the milk expressed from a female breast during an expression session by way of a vacuum pressure sensor. The invention further relates to a method of determining the milk volume and to a computer program calculating a respective milk volume.

BACKGROUND OF THE INVENTION

WO 2010/095133 A1 refers to a device and a method for measuring an amount of breast milk suckled during a breastfeeding session, the device including a mechanism for determining the change in volume of a breast during the breastfeeding session (before breastfeeding and after breastfeeding), and a calculation unit for calculating therefrom the quantity of milk suckled during the breastfeeding session.

US 2015/0112298 A1 discloses a breastfeeding device having a microprocessor having a memory embedded therein that can be pre-programmed to have a plurality of different sucking cycles interspersed with periodic pauses. These different cycles and pauses allow for an accurate modeling of a woman breastfeeding a child. In addition, this system and process can also result in a pre-programmable breastfeeding pump, which creates a preset time for initialization and a preset schedule of a series of events for breastfeeding over a period of time such as over a 24 hour or 30 hour period of time so that the user can automatically use the breast pump without having to use any of the keys on the keyboard of the device. In at least one embodiment, the device including any software which can be programmed thereon, is configured to mimic or model itself towards a suction pattern of a child.

SUMMARY OF THE INVENTION

It is an object of the present invention to provide an improved breast pump which allows easy monitoring the volume of milk expressed by the breast pump, thus ensuring a constant milk volume and avoiding premature drops in milk volume.

In a first aspect of the present invention a breast pump for extracting milk from a female breast is presented, comprising an expression kit, a container connected to the expression kit, and a vacuum unit connected to the expression kit, wherein the combined volumes of the expression kit, the container, the vacuum unit and the connections thereof define a system air volume, a control unit for receiving a sensor signal of the vacuum pressure sensor and a processor for calculating a respective milk volume based on the sensor signal, and a vacuum pressure sensor configured to determine volume changes in the system air volume in response to changes in vacuum pressure.

In a further aspect of the present invention a method for determining the amount of milk expressed from a female breast by a breast pump is presented, comprising the step of determining volume changes in the system air volume in response to changes in vacuum pressure.

In yet a further aspect of the invention a computer program is presented comprising program code means for causing a computer to carry out the steps of the aforementioned method when said computer program is carried out on a computer.

Use of a sensor measuring the increase in vacuum pressure during expression is a very precise method for determining the milk volume expressed from a female breast. A lactating woman using the inventive breast pump has no effort in monitoring the milk volume, remembering the last session, accounting the sessions or making calculations by herself. Monitoring of the milk volume is carried out by the breast pump. The user is informed about the success of the expression and can relax thus making the expression even more effective. The use of a control unit allows effective monitoring of the milk volume based on a completely automatic process without the necessity of complicated operation by the user.

Preferred embodiments of the invention are defined in the dependent claims. It shall be understood that the claimed method has similar and/or identical preferred embodiments as the claimed device and as defined in the dependent claims.

Preferably the vacuum pressure sensor is arranged in the system air volume or is in air-ducting connection to the system air volume. By this arrangement the accuracy of the measurement is ensured.

According to a preferred embodiment of the invention a hygienic barrier, in particular a diaphragm with a porous membrane is arranged between the expression kit and the vacuum unit. By way of this a hygienic operation of the breast pump is possible without milk entering the pump unit. Thus the cleaning effort for the breast pump is restricted to the funnel and the hygienic barrier. The pump unit is not in contact with the milk and thus has not to be disassembled and cleaned.

The change in air volume is preferably defined by $$\Delta V = (t_1 - t_2) * Q_0 \frac{p_{min}}{(p_{min} - p_0) \mathrm{Log}\left[\frac{p_0 \, (p_1 - p_{min})}{p_1 \, (p_0 - p_{min})}\right]},$$

wherein $p_1$ is the sensor signal received from the vacuum pressure sensor ( ) and wherein the parameters $p_{min}$, $p_0$ and $Q_0$ are known. This leaves the vacuum pressure being the only variable which has to be determined by the sensor. Any other parameter is known. The measurement thus is very precise and only depends on one source of potential error.

According to an embodiment of the invention the breast pump can further comprise a vacuum release valve. This release valve helps operating the breast pump with a hygienic barrier between the expression kit and the pump unit.

In an especially preferred embodiment of the invention the breast pump further comprises a flow sensor for measuring the milk flow from the expression kit to the container. This combination can improve accuracy of the measured values and thus of the calculated milk volume.

In an advantageous embodiment of the invention an orifice is arranged between the housing and the container. By way of the orifice, a delay in the evacuation of the container and a deviation from the expected target pressure is achieved, thus resulting in a reduced power demand of the vacuum unit.

According to an alternative preferred embodiment a valve is arranged between the housing and the container, in particular a one-way-valve like a duck bill valve or a flap valve. The valve allows another possibility to reduce power consumption of the vacuum unit.

Advantageously, the valve is configured to close at a predetermined pressure difference between the housing and the container. Thus, the power demand of the vacuum source is reduced and further the milk volume expressed can be calculated based on a different parameter additionally to the change in vacuum pressure during expression.

Preferably the breast pump comprises a user interface including one or more of a display, a speaker, a vibrational element, an actuating element. An interface can convey information to the user of the breast pump thus calming the user down by reporting a successful session. Various possibilities to convey the information can include displaying parameters on a display, or emitting a vibrational or audio signal when a desired milk volume is exceeded. Actuating elements allow easy manipulation of the breast pump like turning the device on or off.

Advantageously the vacuum pressure sensor can be configured to determine pressure changes during a vacuum stroke of the vacuum unit, during a vacuum release stroke of the vacuum unit or in a single stroke modus.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE EMBODIMENTS

Figure 1:
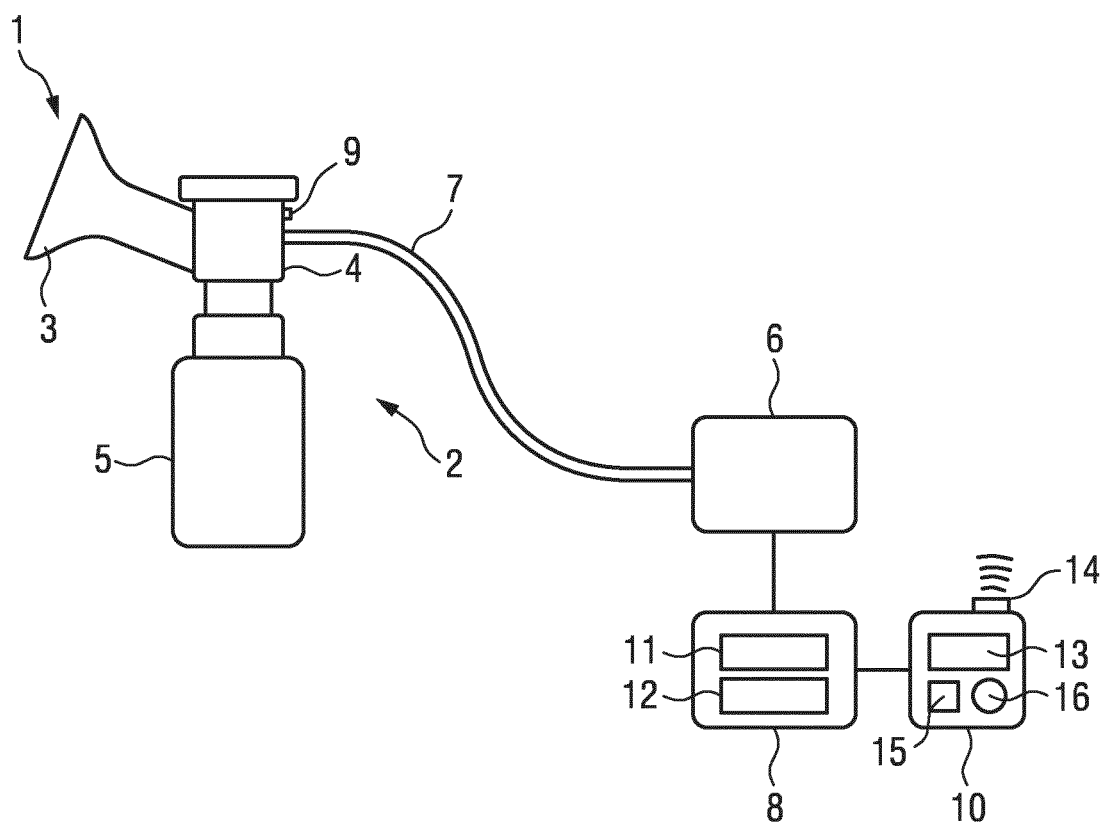
FIG. 1 shows a schematic view of a breast pump according to the invention.

FIG. 1 shows in a very schematic illustration an embodiment of a breast pump 1 suitable for the invention. Lactating women need to regularly express milk to maintain a good milk supply. Without expressing milk regularly, the milk supply is liable to drop. For expressing milk from the female breast, commonly electric breast pumps 1 are used. The embodiment of the breast pump 1 comprises an expression kit 2 with a funnel 3 which is designed to receive a female breast therein. The funnel 3 is coupled to a housing 4, as is a container 5 which is to receive the milk expressed from the female breast.

A vacuum unit 6 is connected to the expression kit 2 by way of a pipe 7. The vacuum unit 6 exerts a suction force to the breast thus sucking milk from the breast by applying a vacuum to the nipple. This process is analogous to the sucking action of a baby during breast feeding.

Electrical breast pumps 1 can be split into two groups. One group of known breast pumps 1 is equipped with a hygienic shield between the vacuum unit 6 and the breast, while the other group lacks this feature. The latter ones comprise a one-way valve which can be housed in the housing 4 to avoid breast milk from flowing back to the funnel 3. Alternatively, the housing 4 can contain a diaphragm or membrane to establish a vacuum or air tight interface between the funnel 3 and the container 5 to prevent milk from entering the vacuum system. Most breast pumps 1 are equipped with a silicone membrane between the vacuum unit 6 and the breast. The vacuum produced by the vacuum unit 6 causes the membrane to move upwards, thereby expanding the air in the funnel 3 in which the breast is positioned. This expansion creates the required vacuum at the breast for the expression of milk therefrom. When the vacuum is released the membrane will move to its rest position again. Thus the vacuum at the vacuum unit 6 is indirectly causing the vacuum at the breast.

When milk is expressed from the breast the milk flows through the funnel 3 via the housing 4 to the container 5. While the container 5 fills, air needs to escape since the available volume is filled by the expressed milk. This air will leak out of the container 5 via a leakage feature between the container 5 and the funnel 3.

A general problem of expressing milk by way of an electrical breast pump 1 is the effort a user has to take to keep count of the milk expressed from the breast. The invention is directed to a new way of determining the expressed milk volume without relying on or requiring the user inputting the amount of milk expressed herself.

Currently a lactation expert would require input from the user of an electric breast pump 1 to keep track of the success rate of the expression. The risk of the user forgetting to monitor the amount is quite high. Besides, the effort for keeping track is high. Due to this lack of correct milk volume data the user is at risk that the milk supply will drop, while the lactation expert is unable to correct the expression schedule timely. Further to this the lactating woman can be quite insecure about the milk supply she has. This insecurity can be relieved by giving feedback to the woman via the breast pump or its peripherals.

In the following the inventive concept that will enable the user to leave the administrative task of keeping track of expressed volume to the electric breast pump will be described.

To allow keeping track of the milk volume which is expressed during a session, a sensor is required which is arranged in the air volume of the breast pump 1. The air volume of the breast pump 1 is defined as the sum of the air volumes of the housing 4, the container 5, the vacuum unit 6 and the connecting pipes 7. Sensors known from the state of the art can e.g. be airflow sensors in the vacuum path or current measurement sensors on the electric motor of the vacuum unit 6. The present invention deals with a pressure sensor in the vacuum path. In the following description a vacuum pressure sensor which is preferably arranged in the housing 4 or in the vacuum unit 6, in any case however in the vacuum air volume or in air-ducting connection herewith, is described.

The basic measurement principle behind the calculation is the observation that in a closed volume of air the pressure will rise when fluid entering the system displaces air. When milk from the female breast fills the container 5, the air in the system will be compressed resulting in a higher pressure. The increase of the pressure is a measure for the milk volume entering the system. To calculate the milk volume the performance of the vacuum unit 6 should be known. Generally, the flow-pressure curve of a vacuum unit is typically part of the specifications of the vacuum unit 6 and thus known as such, but the curve can also be determined during production. Especially the latter method will result in a very precise curve and thus in very precise measurements later.

The invention can be used for breast pumps with a hygienic barrier in form of a membrane or diaphragm as well as for breast pumps without a hygienic barrier between the milk and the vacuum unit. However, the use of a closed system with a hygienic diaphragm will be easier to handle due to the closed air volume inside the breast pump 1. Open systems can be handled, too, when the vacuum has been built up and the system is closed to the environment by air-tight placement of the breast in the funnel 3. The values measured by the vacuum pressure sensor can then be used to determine the air volume in the system which in turn is dependent on the milk volume expressed from the female breast and collected in the container 5.

The thus determined amount of milk can be stored in a control unit 8 which is connected to the vacuum unit 6. To improve the effectiveness of expression, the values can be conveyed to the user of the breast pump 1 e.g. by way of a user interface 10 or via a connection to a separate device (not shown) e.g. via wireless connection to the cloud or to a smart device like a mobile phone. To see the expression session being successful will calm down the user and help to make the session even more effective by inducing a relaxed feeling and security about the success. The user interface 10 can for example comprise a display 13 to show the amount of milk expressed during the session, a speaker 14 for a voice feedback, a vibrational unit 15 for a vibrational signal e.g. announcing a certain milk volume which has ben expressed, and one or more actuating elements 16 like a Start-/Stop-button.

In the preferred embodiment according to FIG. 1, a vacuum/air tight interface between the funnel 3 and the container 5 is described exemplary. A one-way valve is not necessary. Instead, the system will contain a vacuum release valve 9 which can for example be integrated in the housing 4. The breast pump 1 comprises a porous membrane as a hygienic barrier to prevent breast milk from entering the vacuum pump. The membrane can also be housed in the housing as described above. The vacuum pressure sensor is arranged between the porous membrane and the vacuum unit 6. For example, the vacuum pressure sensor can be arranged in the housing 4, in the pump unit 6 or in the connecting pipe 7.

At the start of the expression session, the vacuum unit 6 is operated in a stimulation phase with short vacuum cycles. This is physiologically necessary to stimulate the milk flow. The vacuum pressure sensor will measure the change of the vacuum pressure, which will increase during this phase. This value can directly be used to calculate a vacuum system air volume or starting volume.

After the stimulation phase the milk begins to flow and fills the container 5. By this, the speed of increase of the vacuum will rise because the dead air volume contained in the breast pump 1 is decreased. While the speed of increase of the vacuum is a measure of the dead volume, the difference between the start volume and the current volume is a measure for the expressed amount of milk.

The mathematics involved is not very complex but requires a processor 11 in form of a microcontroller with mathematic capabilities for log calculations. The processor 11 is preferably arranged in the control unit 8. It can communicate with the vacuum pressure sensor in the breast pump 1 and with a storage unit 12 which is preferably also housed in the control unit 8.

As a starting point for the mathematics the breast pump 1 can be interpreted as a pump unit 6 emptying an unknown volume V. The parameters of the pump unit 6 are known and are idealized as a linear Q-H curve defined by its maximum flow rate $Q_0$ (in m$^3$/s) and $p_{min}$ (in Pa). This leads to the following equation which can be rewritten to a ordinary differential equation (ODE):

$$\frac{dp}{dt} = \frac{dm}{dt}\frac{RT}{V}$$

$$\frac{dm}{dt} = Q(p)\rho\frac{RT}{V} = Q(p)\frac{p}{RT}$$

$$Q(p) \approx -Q_0\frac{p - p_{min}}{p_0 - p_{min}}$$

It is to be noted that Q(p) is negative due to flow going out. From this follows:

$$\frac{dp}{dt} = -\frac{Q_0}{V}\frac{p(p - p_{min})}{p_0 - p_{min}}$$

The ODE can be solved which leads to:

$$p(t) = p_{min}\left(1 + \frac{p_0 - p_{min}}{p0\left(e^{\frac{p_{min}Q_0 t}{V(p_0 - p_{min})}} - 1\right) + p_{min}}\right).$$

In the ODE, the following values are present: m=mass, ρ=density, V=volume, Q=flow rate, p=pressure, t=time. $p_{min}$ is given by the pump unit's 6 characteristic, as is $Q_0$. $p_0$ denotes the pressure in the beginning and is assumed to be known.

If a vacuum pressure sensor is present it is now possible to measure the time $t_1$ to a certain required vacuum level $p_1$ at the start when there is definitely no milk in the container 5. Using this measurement it is possible to calculate the empty volume $V_1$ as follows:

$$V_1 = t_1 * Q_0 \frac{p_{min}}{(p_{min} - p_0)\text{Log}\left[\frac{p_0}{p_1}\frac{(p_1 - p_{min})}{(p_0 - p_{min})}\right]}.$$

During expression the air volume will reduce as milk is entering the container 5. It is now possible to measure the time needed $t_2$ to get to the same required vacuum level (which will be quicker) and calculate the new volume. However it is also possible to calculate directly the volume difference dV:

$$\Delta V = (t_1 - t_2) * Q_0 \frac{p_{min}}{(p_{min} - p_0)\text{Log}\left[\frac{p_0}{p_1}\frac{(p_1 - p_{min})}{(p_0 - p_{min})}\right]}.$$

A control loop for determining the milk volume could be implemented by measuring multiple vacuum profiles/cycles. This will increase the accuracy because errors are averaged out. The disadvantage of this is that the vacuum profile that is expected will deviate more from the profile that is generated (correcting will take multiple cycles).

Besides this the control loop could be implemented within one vacuum cycle. The control loop would compare a predetermined vacuum profile with the error measured between the expected and the real vacuum. The advantage of this control principle is that the user is less aware of the measurement that is going on, while the vacuum profile is what is expected.

The combination of a vacuum pressure sensor with a flow sensor could improve the accuracy of the measurement, while the variation in pump behavior (flow-pressure curve) and the variation in pressure drop over the porous membrane could be eliminated from the equation.

One of the error factors will be the breast/nipple. The nipple will act somewhat elastic and visco-elastic, but the effect is relative small. An exemplary start volume can be in the order of 175 ml of which 50 ml are dead volume and 125 ml in the empty container 5. The elastic behavior of the nipple will result in a 2 ml volume error which can be partially compensated while it is quite standard. The visco-elastic behavior will result in an additional 2 ml volume error, also this can be estimated and partially compensated. The milk volume expected is in the order of 75 ml. This results in an error of 1 . . . 5%.

While measuring the vacuum stroke is preferred, the measurement could also be performed in the vacuum release stroke. For a multiple stroke pump unit 6 this stroke is typically very short and therefore the accuracy is likely to be smaller. Nevertheless it is possible to measure a vacuum release pressure-time curve. The air volume and therefor also the milk volume information is also part of the sensor signal. The release of the vacuum is typically achieved via a known air restriction. A large air volume corresponding to a small milk volume will result in a slow vacuum release, while a small air volume corresponding to a large milk volume will result in a fast vacuum release. To increase the resolution of this measurement the restriction can temporarily be made quite small leading to a higher resolution.

FIGS. 2A, 2B, 3A and 3B show two alternative embodiments of the invention which are based on the principle of measurement of the changes in vacuum pressure. Both embodiments use a breast pump 1 which has a hygienic barrier 21 to prevent breast milk from entering the vacuum system. The breast pumps 1 each comprise a funnel 3, a housing 4 and a container 5 as described previously with reference to FIG. 1. The breast pumps 1 further are connected to a vacuum unit 6 via a connecting pipe 7. In the connecting pipe 7, a release valve 9 and a pressure sensor 17 and a flow sensor 18 are present. Alternatively, the release valve can be arranged in the vacuum unit 6.

Figures 2A, 2B:
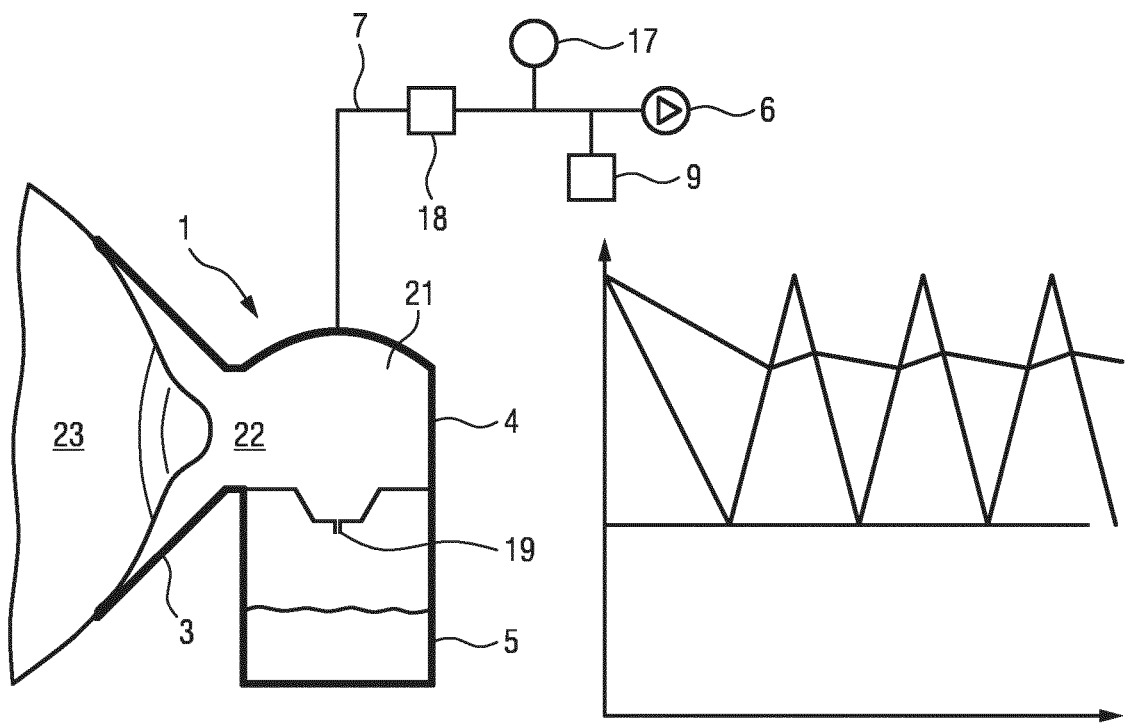
FIGS. 2A and 2B show a schematic view of an alternative embodiment of a breast pump according to the invention and a corresponding vacuum profile.
Figures 3A, 3B:
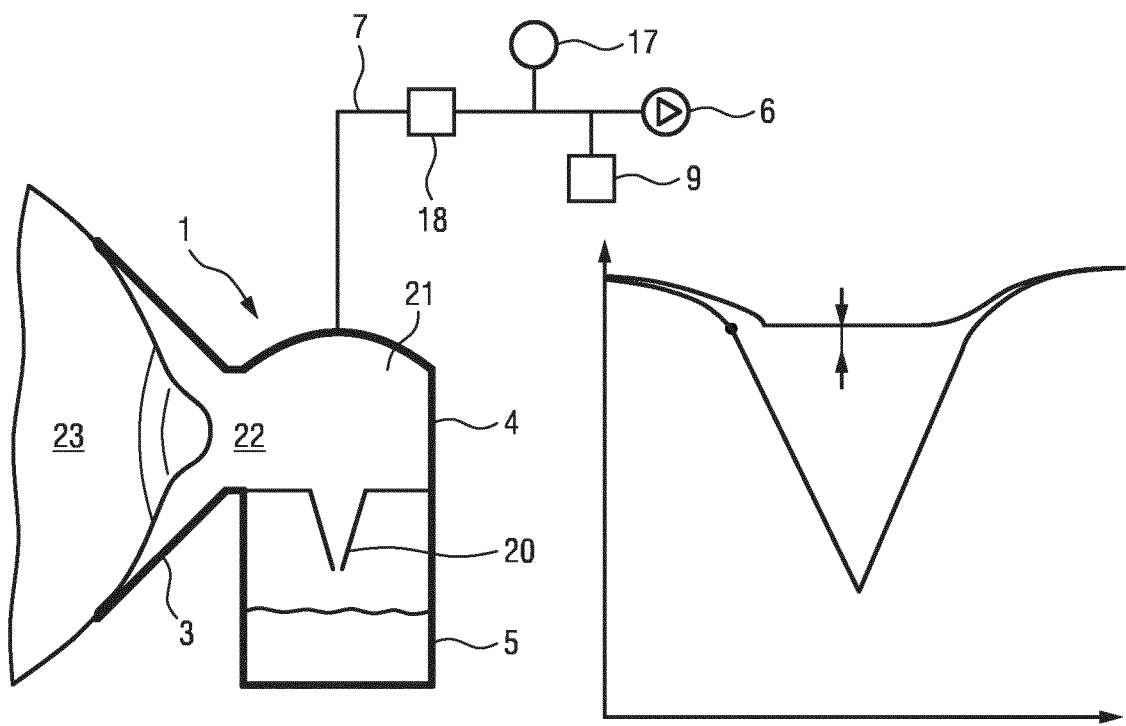
FIGS. 3A and 3B shows a schematic view of yet another embodiment of a breast pump according to the invention and a corresponding pressure diagram.

In contrast to FIG. 1, where the container 5 had to be evacuated to the same vacuum level as a chamber 22 at the breast 23 in the funnel 3, the embodiments according to FIGS. 2A and 3A provide a solution which allows a minor vacuum at the container 5, which results in a decrease in power demand at the vacuum source.

In FIG. 2A, a small inlet orifice 19 is provided at the entry of the container 5. The small inlet orifice 19 causes a delay in the vacuum of the container 5. This delay will result in a deviation from the expected target vacuum value. The deviation is then a measure for the amount of milk in the container 5.

FIG. 2B shows a respective diagram of the pressure measured at the breast 23 in the chamber 22, which is represented by the lower of the two curves of FIG. 2B. The upper curve represents the pressure in the container 5. The latter does not reach the base line of FIG. 2B representing the expected target pressure. Thus, the power demand per cycle is not as high as in the breast pump 1 according to FIG. 1.

In FIG. 3A, another alternative embodiment is shown which features a duck bill valve 20 instead of the small inlet orifice 19 of FIG. 2B. The duck bill valve 20 is configured to close at a pressure difference of e.g. approximately 10 mbar. During the time in which the vacuum source 6 evacuates the chamber 22 in the funnel 3 and the container 5, the milk volume is measured. Due to the duck bill valve 20 also containing an orifice, a pressure difference will occur between the breast chamber 22 and the container 5 which will cause the duck bill valve 20 to close. Thus, after the valve 20 is closed, only the breast chamber 22 has to be evacuated. As soon as the vacuum is released, the duck bill valve 20 opens again. The time required to reset the vacuum system of breast pump 1 to atmospheric pressure is a measure for the milk volume in the container 5.

The vacuum diagram of FIG. 3B shows the pressure difference at which the duck bill valve 20 is closed. The resulting vacuum is significantly lower than the expected vacuum level without closed valve 20. The resulting power demand for the vacuum unit 6 is lower, thus resulting in less wear, less noise and less power consumption. Alternatively, also a flap valve may be used.

Alternatively to these preferred embodiments the invention can also used with a single stroke principle that does not use a release valve. This would require a large stroke volume to compensate for the dead volume in the container 5. Besides, the breast pump 1 can be operated without a silicone hygienic barrier as mentioned above. The silicone hygienic barrier will need to make quite a large stroke to compensate for the large dead volume in the container 5 when empty. With a silicone hygienic barrier the milk volume and the pressure in the pipe 7 at the pump unit 6 side has a direct link to the pressure in the funnel 3 via the stiffness of the silicone hygienic barrier.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A breast pump for extracting milk from a female breast comprising:
   a housing, including a vacuum release valve integrated in the housing,
   an expression kit, a container connected to the expression kit, and a vacuum unit connected to the expression kit via an air-ducting connection, wherein a system air volume is defined as the sum of the air volumes of the expression kit, the housing, the air-ducting connection, the container, and the vacuum unit, a vacuum pressure sensor, and a control unit for receiving a sensor signal of the vacuum pressure sensor and comprising a processor for using the received sensor signal to determine changes in the system air volume in response to changes in vacuum pressure and calculate therefrom a milk volume expressed from the female breast and collected in the container, and wherein the system air volume is dependent on the milk volume expressed from the female breast and collected in the container.

2. The breast pump according to claim 1, wherein the vacuum pressure sensor is arranged in the system air volume.

3. The breast pump according to claim 1, wherein a diaphragm with a porous membrane is arranged between the expression kit and the vacuum unit to prevent milk from entering the pump unit.

4. The breast pump according to claim 1, wherein the change in the system air volume is defined by $$\Delta V = (t_1 1 t_2) * Q_0 \frac{p_{min}}{(p_{min} - p_0) \mathrm{Log}\left[\frac{p_0}{p_1} \frac{(p_1 - p_{min})}{(p_0 - p_{min})}\right]},$$

wherein p1 is the sensor signal received from the vacuum pressure sensor and wherein the parameters pmin, p0 and Q0 are known.

5. The breast pump according to claim 1, further comprising a vacuum release valve.

6. The breast pump according to claim 1, further comprising a flow sensor for measuring the milk flow from the expression kit to the container.

7. The breast pump according to claim 1, wherein an orifice is arranged between the housing and the container.

8. The breast pump according to claim 1, wherein a one way duck bill valve or a flap valve is arranged between the housing and the container.

9. The breast pump according to claim 8, wherein the valve is configured to close at a predetermined pressure difference between the housing and the container.

10. The breast pump according to claim 1, further comprising a user interface including one or more of a display, a speaker, a vibrational element, an actuating element.

11. The breast pump according to claim 1, wherein the vacuum pressure sensor is configured to determine pressure changes during a vacuum stroke of the vacuum unit, during a vacuum release stroke of the vacuum unit or in a single stroke modus.

12. A method for determining the amount of milk expressed from a female breast by a breast pump according to claim 1, comprising the steps of:

operating the vacuum unit in a stimulation phase utilizing short vacuum cycles;

measuring, by a processor, the change in vacuum pressure by a vacuum pressure sensor;

calculating, by the processor, a starting system air volume;

determining, by the processor, volume changes in the system air volume in response to changes in vacuum pressure; and determining, by said processor, a measure of the expressed amount of milk as the difference between the starting system air volume and a current system air volume by said processor.

13. A breast pump for extracting milk from a female breast comprising:

a housing, an expression kit, a container connected to the expression kit, a vacuum unit connected to the expression kit via an air-ducting connection, wherein a system air volume is defined as the combined air volumes of the expression kit, the container, the vacuum unit and the air-ducting connection, a flow sensor for measuring a milk flow from the expression kit to the container, a vacuum pressure sensor arranged in the vacuum unit, and a control unit for receiving a sensor signal of the vacuum pressure sensor and comprising a processor for using the received sensor signal to determine the system air volume and calculate therefrom a milk volume expressed from the female breast and collected in the container, wherein the processor is configured to determine volume changes in the system air volume in response to changes in vacuum pressure, wherein the system air volume is dependent on the milk volume expressed from the female breast and collected in the container, and wherein the vacuum pressure sensor is configured to determine pressure changes during one of a vacuum release stroke of the vacuum unit or in a single stroke modus.

14. The breast pump according to claim 13, further comprising a user interface including one or more of a speaker, a vibrational element, an actuating element.

15. The breast pump according to claim 13, further comprising a wireless interface.

16. A breast pump for extracting milk from a female breast comprising:

an expression kit, a container connected to the expression kit, and a vacuum unit connected to the expression kit via a first connector, wherein the combined volumes of the expression kit, the container, the vacuum unit and the first connector thereof define a system air volume, a flow sensor for measuring a milk flow from the expression kit to the container, a small inlet orifice located at the entry of the container arranged between the housing and the container, wherein the small inlet orifice causes a deviation from an expected target vacuum value which is a measure of the amount of milk in the container, a vacuum pressure sensor arranged in the first connector, and a control unit for receiving a sensor signal of the vacuum pressure sensor and comprising a processor for using the received sensor signal to determine the system air volume and calculate therefrom a milk volume expressed from the female breast and collected in the container, wherein the processor is further configured to determine volume changes in the system air volume in response to changes in vacuum pressure, wherein the system air volume is dependent on the milk volume expressed from the female breast and collected in the container, and wherein the vacuum pressure sensor is configured to determine pressure changes during a vacuum stroke of the vacuum unit.

17. The breast pump according to claim 16, further comprising a user interface including one or more of a speaker, a vibrational element, an actuating element.

18. The breast pump according to claim 16, further comprising a wireless interface.

* * * * *